United States Patent [19]

Goto et al.

[11] 4,433,017

[45] Feb. 21, 1984

[54] THERMALLY REACTIVE WATER-SOLUBLE BLOCKED URETHANE PREPOLYMER

[75] Inventors: Sumio Goto, Moriyama; Takeshi Doi, Omihachiman; Kazuo Sato, Kyoto, all of Japan

[73] Assignee: Dai-Ichi Kogyo Seiyaku Co., Ltd., Kyoto, Japan

[21] Appl. No.: 418,121

[22] Filed: Sep. 14, 1982

[30] Foreign Application Priority Data

Sep. 17, 1981 [JP] Japan .................. 56-148364
Oct. 13, 1981 [JP] Japan .................. 56-164850

[51] Int. Cl.$^3$ ................... C08G 18/80; C08F 8/30
[52] U.S. Cl. ......................... 528/45; 8/115.6; 8/192; 156/330; 525/124; 528/71; 528/73; 528/75; 528/499
[58] Field of Search .................. 528/45, 71, 73, 75

[56] References Cited

U.S. PATENT DOCUMENTS

| | | | |
|---|---|---|---|
| 4,098,933 | 7/1978 | Burkhardt et al. | 528/45 |
| 4,119,602 | 10/1978 | Isgur et al. | 528/45 |
| 4,284,544 | 8/1981 | Wegner et al. | 528/45 |
| 4,314,922 | 2/1982 | Lehner et al. | 528/45 |
| 4,322,327 | 3/1982 | Yoshimura et al. | 528/45 |
| 4,349,655 | 9/1982 | Leitner et al. | 528/45 |

*Primary Examiner*—H. S. Cockeram
*Attorney, Agent, or Firm*—Millen & White

[57] ABSTRACT

A thermally reactive water-soluble urethane prepolymer having a plurality of masked isocyanate groups capable of regenerating free isocyanate groups at an elevated temperature, said urethane prepolymer having the formula:

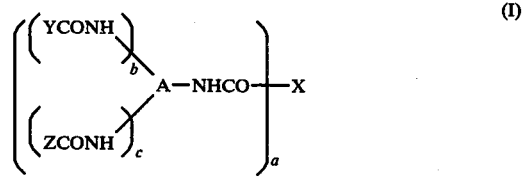

wherein
A is an organic bridging group having a valency from 3 to 5,
X is the residue of an active hydrogen compound having 2 to 4 active hydrogen atoms with removal of said active hydrogen atoms,
Y is a masking group for isocyanate group,
Z is the residue of a compound having at least one active hydrogen atom and at least one ionizable group with removal of said active hydrogen atom,
a is an integer from 2 to 4, and
b and c are such that the sum of b+c equals 2 to 4 and the products of ab and ac are at least 2 and at least 1, respectively.

12 Claims, No Drawings

THERMALLY REACTIVE WATER-SOLUBLE BLOCKED URETHANE PREPOLYMER

BACKGROUND OF THE INVENTION

It is well-known that a urethane prepolymer containing free isocyanate groups may be rendered nonreactive by reacting the prepolymer with a masking agent for isocyanate groups. The resulting blocked prepolymer is normally inert but may regenerate reactive free isocyanate groups upon heating. This permits the preparation of aqueous systems of urethane prepolymers.

Aqueous dispersions or emulsions of urethane prepolymers have hitherto been prepared by ball milling or emulsifying a hydrophobic blocked prepolymer in water, or by introducing a hydrophilic group such as an ionizable group or a polyoxyethylene chain into the blocked prepolymer molecule to obtain a self-emulsifying prepolymer.

Experiments have shown that these aqueous systems are not satisfactory with respect to properties such as stability against phase separation, compatibility with other water-soluble polymeric substances, water resistance and the like.

Therefore, it is a main object of the present invention to provide a thermally reactive water-soluble urethane prepolymer which is freely soluble or dispersible in water without phase separation, compatible with other water-soluble polymeric substances in an aqueous system and gives, when reacted at an elevated temperature, a polyurethane composition having improved properties.

Other objects and advantages of the present invention will become apparent from the description hereinafter.

DESCRIPTION OF THE INVENTION

According to the present invention, there is provided a thermally reactive water-soluble urethane prepolymer having a plurality of masked isocyanate groups capable of regenerating free isocyanate groups, said urethane prepolymer having the formula:

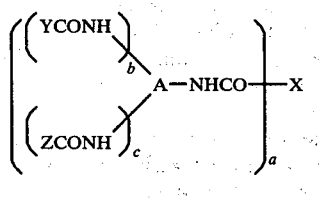

wherein
A is an organic bridging group having a valency from 3 to 5,
X is the residue of an active hydrogen compound having 2 to 4 active hydrogen atoms with removal of said active hydrogen atoms,
Y is a masking group for isocyanate group,
Z is the residue of a compound having at least one active hydrogen atom and at least one ionizable group with removal of said active hydrogen atom,
a is an integer from 2 to 4, and
b and c are such that the sum b+c equals 2 to 4 and the products ab and ac are at least 2 and at least 1, respectively.

In other terms, the prepolymer of the above formula (I) has at least two masked isocyanate groups and at least one ionizable group per molecule, and has no free isocyanate group.

The blocked prepolymer of the formula (I) may be prepared by the steps of
(a) preparing a urethane prepolymer of the formula:

$$[(OCN)_{b+c}A-NHCO]_{a}X \qquad (II)$$

wherein all symbols are as defined above by reacting an appropriate polyisocyanate having 3 to 5 isocyanate groups and an active hydrogen compound of the formula $X-(H)_a$,
(b) preparing a partially blocked urethane prepolymer of the formula:

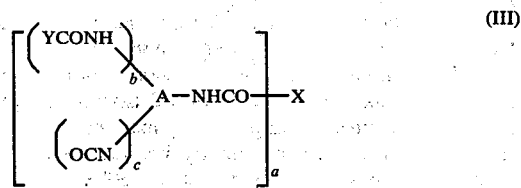

wherein all symbols are as defined above, by reacting the prepolymer of the formula (II) and a masking agent of the formula Y-H, and
(c) reacting the resultant prepolymer of the formula (III) with a compound of the formula Z-H to obtain the prepolymer of the formula (I).

Step (a)

Examples of polyisocyanates having 3 to 5 isocyanate groups include tris-(isocyanatohexyl)-biuret, triphenylmethanetriisocyanate, polymethylenepolyphenylpolyisocyanate, adducts of a diisocyanate such as hexamethylenediisocyanate, xylylenediisocyanate, isophoronediisocyanate, tolylenediisocyanate and diphenylmethanediisocyanate with a low molecular weight polyol such as trimethylolpropane, trimers of hexamethylenediisocyanate and/or tolylenediisocyanate and the like.

Examples of active hydrogen compounds of the formula $X-(H)_a$ are as follows:
(1) polyols such as ethylene glycol, butylene glycol, propylene glycol, neopentyl glycol, diethyleneglycol, triethylene glycol, glycerine, trimethylolpropane, trishydroxyethylisocyanurate and the like;
(2) polyamines such as ethylenediamine, hexamethylenediamine, phenylenediamine, distyrenetriamine, and polyamide-polyamines of these amines and a polycarboxylic acid such as adipic acid, maleic acid, phthalic acid, terephthalic acid and dimer acid;
(3) amino alcohols such as ethanolamine, diethanolamine, triethanolamine and propanolamine,
(4) polyester-polyols of a polycarboxylic acid such as adipic acid, succinic acid, maleic acid, fumaric acid, phthalic acid, terephthalic acid and dimer acid, and a polyol such as ethylene glycol, diethylene glycol, propylene glycol, butylene glycol, neopentyl glycol, hexylene glycol, trimethylolpropane and glycerine-tris-hydroxyethylisocyanurate, and lactone-polyester-polyols obtained by the ring-cleaving polymerization of caprolactone;
(5) polybutadiene-polyols such as polybutadiene glycol and copolymers thereof with a vinyl monomer such as styrene and acrylonitrile;

(6) polychloroprene-polyols such as polychloroprene glycol and copolymers thereof with a vinyl monomer such as styrene and acrylonitrile;

(7) polyether-polyols such as homopolymers and interpolymers (block or random) of a $C_3$ or $C_4$ alkylene oxide, copolymers of a $C_3$-$C_4$ alkylene oxide with ethylene oxide, adducts of a $C_2$-$C_4$ alkylene oxide with a compound of the above (1), (2) or (3), or a polyphenol such as bisphenol A and 4,4'-dihydroxydiphenylsulfone; and (8) other active hydrogen compounds such as polythioethers, polyacetals, polyester-amides and acrylic polyols.

The active hydrogen compounds from (4) to (7) above should have a molecular weight less than 5,000, preferably less than 2,000.

The reaction between a polyisocyanate and an active hydrogen compound is well-known in the art. The ratio of NCO equivalent/H atom equivalent should be substantially equal to the number of isocyanate groups possessed by the starting polyisocyanate employed. The reaction may be carried out by heating two reaction components at a temperature below 150° C., preferably from 60° to 120° C. for a sufficient length of time.

Step (b)

Examples of masking agents of the formula Y-H include phenols such as phenol, chlorophenol, cresol, p-t-butyl phenol, p-sec.-butylphenol, p-sec.-amylphenol, p-octylphenol and p-nonylphenol; secondary or tertiary alcohols such as isopropanol and t-butanol; oximes such as acetoxime, methyl ethyl ketoxime and cyclohexanone oxime; lactams such as ε-caprolactam and δ-valerolactam; active methylene compounds such as dialkyl malonate, acetylacetone and alkyl acetacetate, heterocyclic hydroxyl compounds such as 3-hydroxypyridine, 8-hydroxyquinoline and 8-hydroxyquinaldine; and bisulfites such as sodium bisulfite and potassium bisulfite.

The molar ratio of the masking agent to the prepolymer (II) should be such that at least two free isocyanate groups per molecule are blocked while at least one free isocyanate group per molecule remains unblocked.

The reaction between the prepolymer (II) and a masking agent may be carried out at a temperature from 50° to 90° C. optionally in an inert solvent and in the presence of a catalyst such as triethylamine and dibutyltin dilaurate.

Step (c)

The compound which introduces the group Z into the molecule of the partially blocked urethane prepolymer (III) should have at least one functional group having an active hydrogen atom such as a primary or secondary amino group of a hydroxyl group. The compound should also have at least one ionizable group such as a carboxylate group, sulfonate group and a quaternary ammonium group or a precursor thereof.

Examples of these compounds include amino sulfonic acids such as taurine, N-methyltaurine, N-butyltaurine and sulfanilic acid; amino carboxylic acids such as glycine and alanine; hydroxy carboxylic acids such as 2-hydroxyethanesulfonic acid and phenol-2,4-disulfonic acid; hydroxy carboxylic acid such as glycolic acid, salicylic acid and p-hydroxybenzoic acid; hydroxyl group-containing tertiary amines such as N,N-dimethylethanalamine, N,N-dimethylpropanalamine, N,N-dimethyl-β-hydroxyethylaniline, α-hydroxyethylpyridine, β-hydroxyethylquinoline and N-hydroxyethylpiperidine; and amino group-containing tertiary amines such as N,N-dimethylhydrazine, N,N-dimethylethylenediamine, N,N-dimethylpropylenediamine and α-aminopyridine.

It is preferable for these compounds to react with the prepolymer (III) in the form of a salt with a base such as sodium hydroxide, sodium carbonate, potassium hydroxide, potassium carbonate, ammonia, ethylamine, triethylamine, dimethylamine, pyridine, mono-, di- or triethanolamine in case of a carboxylic acid and sulfonic acid, or with a quaternizing agent such as hydrochloric acid, sulfuric acid, nitric acid, formic acid, acetic acid, lactic acid, chloroacetic acid, methyl iodide, ethyl bromide or dimethyl sulfate in the case of a tertiary amine. Alternatively, the salt-forming or quaternization reaction may be performed after the reaction with a precursor.

The step (c) may be carried out by reacting the prepolymer (III) with a solution of said compound at a temperature of 20° to 60° C.

The resulting reaction mixture containing the thermally reactive water-soluble urethane prepolymer of the present invention may find a number of important uses. As an example of such uses, although not limited thereto, the prepolymer of the present invention may be used for bonding various organic polymeric materials themselves or to other materials such as glass, ceramics and metals. Such organic polymeric materials include natural products such as cellulose, wool, silk, leather and natural rubber; and semisynthetic or synthetic polymers such as synthetic resins, synthetic fibers, synthetic rubbers, cellulose derivatives and natural rubber derivatives. Particularly advantageous are polyester/rubber, nylon/rubber, nylon/polyvinyl chloride, polyvinyl chloride/cotton and polypropylene/paper. The terms "nylon" and "polyester" used herein include fibers, yarns, cords, fabrics, nonwoven fabrics, knittings, sheets, felt, films and other shaped articles made therefrom. Also, the term "polyvinyl chloride" includes flexible or rigid sheets, tubes, films, boards and other shaped articles made therefrom. For example, a polyester fabric is soaked in or coated with a solution of the prepolymer of the present invention and dried at a temperature of 80° to 120° C. After this treatment, the fabric may be heat bonded to a flexible polyvinyl chloride sheet by heat pressing together at a temperature of about 150° to 250° C.

The water-soluble urethane prepolymer of the present invention may be combined with other water-based adhesive compositions such as polyepoxy compounds, ethyleneurea, SBR latex, NBR latex, melamine resins, phenol resins, urea resins, resorcinol-formaldehyde resins, acrylic emulsions, polyurethane emulsions, starch, gelatin, carboxymethylcellulose and polyvinyl alcohol. Other additives such as plasticizers, pigments and fillers may also be added to the adhesive composition.

Alternatively, the shaped articles such as nylon fabrics to be heat bonded may be pretreated with the water-soluble prepolymer of the present invention by soaking the fabric in an aqueous solution of the prepolymer, drying the fabric at a temperature of 100° to 120° C. for 5 to 10 minutes, and then optionally heating the dried fabric at a temperature of 150° to 250° C. This pretreatment also improves the bond strength to other shaped articles subsequently bonded to the nylon fabric by means of conventional bonding technique. A pick-up from 0.5 to 10% by weight on dry basis is preferable for the pretreatment of nylon fabric.

As a further example, the water soluble urethane prepolymer of the present invention may be reacted with a water-soluble polymeric substance at an elevated temperature to render it water-insoluble through a cross-linking reaction.

Examples of water-soluble polymeric substances include naturally occurring polymers such as starch (potato, tapioca, wheat, corn etc.,), galactomannan, pectin, agar, irish moss extract, sodium alginate, gum tragacanth, gum arabic, guar gum, tamarid gum, locust bean gum, glue, gelatin and casein; semi-synthetic polymers such as methylcellulose, ethylcellulose, hydroxyethylcellulose, hydroxypropylcellulose, carboxymethylcellulose, soluble starch, carboxymethylstarch; and synthetic polymers such as polyvinyl alcohol, water-soluble acrylic resins, polyacrylamide, polyethylene oxide and the like. The amount of the urethane prepolymer of this invention is generally from 0.1 to 80% by weight of the water-soluble polymeric substance on dry basis.

As a still further example, various textile products may be treated with an aqueous solution of the prepolymer of this invention for the purposes of water-proof treatment, anti-crease treatment, touch-improving treatment, shrink-proof treatment and the like.

In such usages, the water-soluble urethane prepolymer of the present invention is freely soluble or dispersible in an aqueous medium and may be admixed with other water-soluble substances. After applying the solution or dispersion on an article and drying the same at a temperature generally below 120° C., the prepolymer is heated generally at a temperature from 140° to 200° C. to regenerate free isocyanate groups. The regenerated free isocyanate group will then react with an active hydrogen atom to form a urethane or urea linkage in the well-known manner for adhesively bonding various materials, cross-linking water-soluble polymeric substances and other purposes.

To further illustrate the invention, the following examples are presented. Unless otherwise indicated, all parts and percents are by weight.

PREPARATION OF THERMALLY REACTIVE SOLUBLE PREPOLYMERS

EXAMPLE 1

1 mole of trimethylolpropane was reacted with 3 moles of tolylenediisocyanante (mixture of 2,4- and 2,6-isomers at 80:20) to obtain a triisocyanate compound having a free isocyanate group content of 19.2%.

100 parts of the resulting triisocyanate are reacted with 6.9 parts of 1,4-butanediol (molar ratio of NCO/OH=3) at 85° C. for 60 minutes to obtain a urethane prepolymer having a free isocyanate group content of 11.9%. To the resultant reaction mixture were added 2.8 parts of a solution of 7.2 parts of phenol in 21.4 parts of dioxane and 0.2 parts of triethylamine as a catalyst at 50° C. The mixture was gradually heated to 85° C. and reacted at the same temperature for 60 minutes to obtain 135.7 part of a dioxane solution of partially blocked urethane prepolymer having a free isocyanate content of 2.9%.

To the solution was added 27.1 parts of 40% aqueous solution of taurine at 40° C. The mixture was reacted at a temperature from 40° to 50° C. for 30 minutes and then diluted with 462 parts of water to a non-volatile content of 20% 624.8 parts of a stable, semi-transparent, homogeneous aqueous solution were obtained.

EXAMPLE 2

To a mixture of 100 parts of tris-(isocyanatohexyl)-biuret and 30 parts of dioxane were gradually added 39.5 parts of a solution of 5.6 parts of ethylenediamine (the molar ratio of $NCO/NH_2=3$) in 22.8 parts of dioxane at 25° C. under cooling. After the exotherm, the mixture was heated at 75° C. for 15 minutes to obtain 179.5 parts of a solution containing the resulting urethane prepolymer having a free isocyanate content of 14.51%.

To the solution were added 52 parts of a solution of 30.9 parts of ε-caprolactam in 21.1 parts of dioxane and 0.21 parts of tetramethylpropylenediamine as a catalyst at 50° C. The mixture was reacted at 35° C. for 90 minutes to obtain 231.71 parts of a solution of partially blocked urethane prepolymer having a free isocyanate content of 3.71%.

To the solution were added 34.3 parts of 40% aqueous solution of taurine at 40° C. The mixture was reacted at a temperature from 40° to 50° C. for 30 minutes and then diluted with 435.1 parts of water to a non-volatile content of 20%. 751.1 parts of homogeneous aqueous solution were obtained.

EXAMPLE 3

50 parts of tris-(isocyanatohexyl)-biuret(free isocyanate group content 23.5%) were reacted with 55 parts ((NCO/OH molar ratio=3) of a polyester-polyol (prepared from 1,6-hexanediol and maleic anhydride, hydroxyl number 95, acid number 1.6) at 85° C. for 60 minutes to obtain 105 parts of a urethane prepolymer having a free isocyanate group content of 7.46%. To the prepolymer were added 13.1 parts of phenol dissolved in 21 parts of dioxane and 0.21 parts of triethylamine as a catalyst at 60° C. The mixture was reacted at 85° C. for 60 minutes to obtain 139.31 parts of a solution of partially blocked urethane prepolymer having a free isocyanate group content of 1.88%.

To the solution were added 17.3 parts of 40% aqueous solution of taurine at 40° C. The mixture was reacted at a temperature of 40° to 50° C. for 30 minutes and then diluted with 260 parts of water to a non-volatile content of 30%. 416 parts of a viscous, transparent solution were obtained.

EXAMPLE 4

50 parts of tris-(isocyanatohexyl)-biuret were reacted with 139.9 parts (NCO/OH molar ratio=3) of polybutadiene glycol (average M.W.=3,000) at 85° C. for 60 minutes to obtain 189.9 parts of a urethane prepolymer having a free isocyanate group content of 4.12%. To the prepolymer were added 12.2 parts of methyl ethyl ketoxime in 57 parts of dioxane at 60° C. The mixture was reacted at 85° C. for 30 minutes to obtain 259.1 parts of a solution of partially blocked urethane prepolymer having a free isocyanate group content of 1.01%. To the solution were added 14.8 parts of 30% aqueous solution of sodium glycinate at 40° C. The mixture was reacted at a temperature of 40° to 50° C. for 30 minutes and diluted with water to a non-volatile content of 30%. 688.5 parts of a viscous, semi-transparent solution were obtained.

EXAMPLE 5

100 parts of tris-(isocyanatohexyl)-biuret were reacted with 6.3 parts (NCO/OH molar ratio=3) at 85° C. for 50 minutes to obtain 106.3 parts of a urethane prepolymer having a free isocyanate content of 14.72%.

To the prepolymer were added 26.4 parts of methyl ethyl ketoxime in 21.2 parts of dioxane at 60° C. The mixture was reacted at 85° C. for 30 minutes to obtain 153.9 parts of a solution of partially blocked urethane prepolymer having a free isocyanate group content of 2.71%.

To the solution were added 25.2 parts of 40% aqueous solution of taurine at 40° C. The mixture was reacted at a temperature of 40° to 50° C. for 30 minutes and diluted with water to a non-volatile content of 30%. 476 parts of a viscous, homogeneous solution were obtained.

EXAMPLE 6

100 parts of polymethylenepolyphenylpolyisocyanate (free isocyanate group content=31.5%) were reacted with 24.4 parts (NCO/OH molar ratio=5) of an ethylene oxide adduct of bisphenol A (2:1 in molar ratio, OH number=35.4) at 85° C. for 30 minutes to obtain 124.4 parts of a urethane prepolymer having a free isocyanate group content of 20.26%.

The resulting prepolymer was then reacted with 72 parts of p-sec.-butylphenol in 62.2 parts of dioxane in the presence of 0.25 parts of triethylamine at 85° C. for 30 minutes to obtain 258.85 parts of a solution of partially blocked urethane prepolymer having a free isocyanate content of 4.0%.

To the solution were added 43.6 parts of 40% aqueous solution of taurine at 40° C. The mixture was then reacted at a temperature of 40° to 50° C. for 30 minutes and diluted with water to a non-volatile content of 25%. 855.4 parts of a semi-transparent, homogeneous solution were obtained.

EXAMPLE 7

100 parts of polymethylenepolyphenylpolyisocyanate were reacted with 25 parts (molar ratio of NCO/OH=5) of a polyether-polyol (average M.W.=500) prepared by addition-reacting glycerine with 50:50 mixture of propylene oxide and ethylene oxide (random) at 85° C. for 30 minutes to obtain 125 parts of a urethane prepolymer having a free isocyanate group content of 20.15%.

The resulting prepolymer was then reacted with 81 parts of p-sec.-butylphenol in 37.5 parts of dioxane in the presence of 0.25 parts of triethylamine at 85° C. for 30 minutes to obtain 243.75 parts of a solution of partially blocked urethane prepolymer having a free isocyanate group content of 2.05%.

To the solution were added 22.4 parts of 40% aqueous solution of taurine at 40° C. The mixture was reacted at a temperature of 40° to 50° C. for 30 minutes and diluted with water to a non-volatile content of 20%. 1,075 parts of a slightly cloudy solution were obtained.

EXAMPLE 8

1 mole of trimethylolpropane was reacted with 3 moles of tolylenediisocyanate (80:20 mixture of 2,4- and 2,6-isomers) to obtain a triisocyanate compound having a free isocyanate group content of 19.2%.

100 parts of the triisocyanate compound were reacted with 4.7 parts (molar ratio of NCO/OH=3) of ethylene glycol at 85° C. for 60 minutes to obtain 104.7 parts of urethane prepolymer having a free isocyanate group content of 12.24%.

The resulting prepolymer was reacted with 50.3 parts of nonylphenol in 20.9 parts of dioxane in the presence of 0.21 parts of triethylamaine at 85° C. for 60 minutes to obtain 176.11 parts of a solution of partially blocked urethane prepolymer having a free isocyanate group content of 3.04%.

To the solution were added 27.9 parts of 40% aqueous solution of taurine at 40° C. The mixture was reacted at 40°–50° C. for 30 minutes and diluted with water to a non-volatile content of 30%. A semi-transparent, homogeneous solution was obtained.

EXAMPLE 9

100 parts of polymethylenepolyphenylpolyisocyanate were reacted with 23.7 parts (molar ratio of NCO/OH=5) of 1,6-hexanediol-maleate glycol (OH number=357, acide number=1.1) at 85° C. for 30 minutes to obtain 123.7 parts of urethane prepolymer having a free isocyanate group content of 20.38%.

The resulting prepolymer was then reacted with 45.7 parts of methyl ethyl ketoxime in 24.7 parts of dioxane at 85° C. for 30 minutes to obtain 194.1 parts of a solution of partially blocked urethane prepolymer having a free isocyanate content of 2.53%.

To the solution were added 27.4 parts of 40% aqueous solution of taurine at 40° C. The mixture was reacted at 40°–50° C. for 30 minutes and diluted with water to a non-volatile content of 30%. A viscous, homogenous solution was obtained.

EXAMPLE 10

100 parts of tris-(isocyanatohexyl)-biuret were reacted wtih 29.4 parts (molar ratio of NCO/OH=3) of 1,6-hexanediol-maleate glycol (OH number=357, acid number=1.1) at 85° C. for 50 minutes to obtain 129.4 parts of urethane 85° C. for 50 minutes to obtain 129.4 parts of urethane prepolymer having a free isocyanate group content of 12.17%.

The resulting prepolymer was reacted with 26.5 parts of phenol in 25.9 parts of dioxane in the presence of 0.26 parts of triethylamine at 85° C. for 60 minutes to obtain 182.06 parts of a solution of partially blocked urethane prepolymer having a free isocyanate content of 3.01%.

To the solution were added 10.9 parts of N,N-diethylethanolamine at 50° C. The mixture was reacted at 85° C. for 60 minutes. To the mixture were added 5.6 parts of acetic acid in 25.9 parts of isopropanol and 331.54 parts of water at 50° C. with stirring. 556 parts of a semi-transparent, homogeneous solution having a non-volatile content of 30% were obtained.

REFERENCE EXAMPLE 1

Ball milling of a fully blocked polyisocyanate

A triisocyanate compound prepared in Example 1 was fully blocked with phenol.

200 parts of this blocked triisocyanate, 10 parts of an anionic surfactant of dialkyl sulfosuccinate type, 2 parts of polyoxyethylene nonylphenol ether (HLB 12), and 394 parts of water were ball milled for 24 hours to obtain an aqueous dispersion having a solid content of 35%. Phase separation was observed after standing for 1 day.

REFERENCE EXAMPLE 2

Self-emulsified partially blocked polyisocyanate 100 parts of polymethylenepolyphenylpolyisocyanate were reacted with 84.4 parts of p-sec.-butylphenol in 50 parts of dioxane in the presence of 0.2 parts of triethylamine at 85° C. for 30 minutes to obtain 234.6 parts of a solution of partially blocked polyisocyanate having a free isocyanate group content of 7.81%.

The solution was reacted with 68.4 parts of 40% aqueous solution of taurine at 40°–50° C. for 30 minutes and then diluted with water to a solid content of 30%.

The resulting cloudy dispersion was allowed to stand for 2 days whereupon sand-like precipitates were observed.

REFERENCE EXAMPLE 3

Emulsion of fully blocked urethane prepolymer 50 parts of tris-(isocyanatohexyl)-biuret were reacted with 55 parts (molar ratio of NCO/OH=3) of 1,6-hexanediolmaleate glycol (OH number=95, acid number=1.6) at 85° C. for 60 minutes to obtain 105 parts of urethane prepolymer having a free isocyanate group content of 7.46%.

This prepolymer was reacted with 17.5 parts of phenol in 21 parts of dioxane in the presence of 0.21 parts of triethylamine at 85° C. for 60 minutes.

143.71 parts of the resulting solution, 10 parts of an anionic surfactant of the dialkyl sulfosuccinate type and 2 parts of polyoxyethylene nonylphenol ether were emulsified in 292.6 parts of water with vigorous stirring to obtain 448.3 parts of an emulsion having a non-volatile content of 30%.

REFERENCE EXAMPLE 4

Bisulfite-blocked soluble urethane prepolymer 21 parts of polyether-diol (average M.W.=2,400) prepared by addition-reacting ethylene oxide with polypropyrene glycol (average M.W.=1,200) were mixed with 56 parts of 1,6-hexanediol/neopentyl glycol/adipate (7:4:10) polyester polyol (OH number 45.1, acid number 2.4), 3 parts of 1,6-hexanediol and 20 parts of hexamethylenediisocyanate. The mixture was reacted at 100° C. for 60 minutes to obtain a urethane prepolymer having a free isocyanate group content of 5.02%.

100 parts of this prepolymer were reacted with 65 parts of 25% aqueous solution of sodium bisulfite at 40°–45° C. for 20 minutes and diluted with water to a non-volatile content of 30%. A cloudy but homogeneous solution was obtained.

EXAMPLE 11

Bonding nylon fabric to PVC sheet

A nylon fabric was soaked in a solution of urethane prepolymer obtained in the preceding examples, squeezed to a pick up of about 2.0% on dry basis, and dried at 100° C. for 10 minutes.

This fabric was placed on a flexible polyvinyl chloride sheet and heat bonded at 150° C. under a pressure of 3 kg/cm² for 3 minutes.

The peel strength of each test specimen of 2.5×10 cm size was determined by a tensile tester.

The results and the flexibility of adhesive layer as well as the stability of solutions are shown in Table I.

TABLE I

| Prepolymer | Peel strength (kg/2.5 cm) | Flexibility | Stability against phase separation |
|---|---|---|---|
| Ex. 1 | 9.7 | fair | good |
| Ex. 2 | 10.5 | " | " |
| Ex. 3 | 13.5 | good | " |
| Ex. 4 | 10.4 | " | " |
| Ex. 5 | 12.3 | fair | " |
| Ex. 6 | 10.7 | " | " |
| Ex. 7 | 9.5 | " | " |
| Ref. 1 | 5.3 | poor | poor |
| Ref. 2 | 3.2 | " | " |
| Ref. 3 | 7.6 | good | fair |

As shown in Table I, the nylon fabric treated with a urethane prepolymer of this invention exhibited an improved peel strength value compared with that treated with conventional aqueous blocked polyisocyanate systems.

EXAMPLE 12

Treatment of nylon cord

A nylon cord was soaked in a solution of urethane prepolymer obtained in the preceding example to a pick up of about 2% on dry basis and then dried at 120° C. for 3 minutes. The dried cord was then soaked in resorcinol-formaldehyde condensate/latex (RFL) to a pick up amount of about 3% on dry basis and heated at 200° C. for 2 minutes.

This cord was embedded in a piece of natural rubber and cured at 150° C. for 30 minutes. The peel strength, drawing strength and flex modulus of the treated cord were compared with control which was treated only with RFL. The results are shown in Table II in terms of an index when the parameter values of control are 100 respectively.

TABLE II

| Prepolymer | Peel strength | Drawing strength | Flex modulus |
|---|---|---|---|
| Ex. 1 | 122 | 98 | 101 |
| Ex. 2 | 143 | 104 | 97 |
| Ex. 3 | 161 | 114 | 84 |
| Ex. 4 | 152 | 128 | 72 |
| Ex. 5 | 135 | 131 | 86 |
| Ex. 6 | 124 | 112 | 105 |
| Ex. 7 | 115 | 115 | 92 |
| Ref. 1 | 108 | 85 | 121 |
| Ref. 2 | 92 | 98 | 103 |
| Ref. 3 | 110 | 117 | 95 |
| Control | 100 | 100 | 100 |

As shown in Table II, the prepolymer of the present invention improves the bonding strength of nylon to natural rubber substantially more than conventional aqueous blocked isocyanate systems.

EXAMPLE 13

Heat bonding of rubber or plastic sheets

A solution of urethane prepolymer of the present invention prepared in the preceding examples having a non-volatile content of 20% was applied on pairs of rubber sheets (1 mm thick), polyethylene terephthalate sheets (0.5 mm thick) of 5×10 cm size in one half area, respectively. Each pair was joined together with adhesive layers facing to each other, pretreated at 100° C. at a pressure of 2 kg/cm² for 10 minutes, and finally heated at 150° C. for 10 minutes.

The peel strength of each test specimen was determined. The results are shown in Table III.

TABLE III

| Prepolymer | Peel strength (kg/5 cm) | | |
|---|---|---|---|
| | rubber | Polyethylene terephthalate | Polypropylene |
| Ex. 1 | 27.1 | 18.6 | 3.7 |
| Ex. 2 | 24.5 | 16.3 | 2.9 |
| Ex. 3 | 28.7 | 19.5 | 3.4 |
| Ex. 4 | 29.9 | 15.7 | 2.6 |
| Ex. 5 | 25.2 | 16.1 | 3.3 |
| Ex. 6 | 30.6 | 21.8 | 3.2 |
| Ex. 7 | 26.8 | 19.4 | 3.2 |
| Ref. 1 | 20.6 | 15.4 | 2.1 |
| Ref. 2 | 20.5 | 13.8 | 2.3 |
| Ref. 3 | 23.3 | 14.2 | 1.9 |

As shown in Table III, the prepolymer of the present invention gives better results than conventional aqueous blocked isocyanate systems.

EXAMPLE 14

Bonding PVC sheet to plywood

A solution of urethane prepolymer prepared in the preceding example and having a non-volatile content of 20% was applied on a 5×10 cm sheet of plywood in one half area. A 5×15 cm sheet of flexible polyvinyl chloride sheet (0.5 mm thick) was applied to the plywood sheet. The composite sheet was dried in an oven at 100° C. for 10 minutes and heat bonded in a hot press at 150° C. under a pressure of 2 kg/cm² for 5 minutes. The peel strength of each test specimen was determined at 180° C. The results are shown in Table IV.

TABLE IV

| Prepolymer | Peel strength at 180° C. (kg) |
|---|---|
| Ex. 1 | 18.5 |
| Ex. 2 | 15.7 |
| Ex. 3 | 17.8 |
| Ex. 4 | 15.9 |
| Ex. 5 | 15.1 |
| Ex. 6 | 19.5 |
| Ex. 7 | 17.4 |
| Ref. 1 | 14.7 |
| Ref. 2 | 11.3 |
| Ref. 3 | 13.4 |

EXAMPLE 15

Cross-linking of polyvinyl alcohol

A 20% aqueous solution of PVA-217 (Kuraray, partially saponified polyvinyl acetate) was mixed with a solution of blocked urethane prepolymer obtained in the preceding example at a ratio of 100:5 on dry basis. The mixture was then cast into a TEFLON coated petri dish, dried at room temperature for 15 hours and then at 60° C. for 4 hours, and finally cured in an oven at 160° C. for 20 minutes to give a film of 0.5 mm thickness. The film was cut into 2×5 cm size and placed in an atmosphere of a constant temperature of 20° C. at a RH of 65%.

The film was then soaked in water having a temperature of 40° C. or in boiling water for 30 minutes, dried at 105° C. for 1 hour, and placed in the above atmosphere for 2 hours. Percent decrease in weight after soaking in water was determined and the change in appearance after soaking was observed. The results are shown in Table V.

TABLE V

| Cross-linking agent | Soaking in water | | | |
|---|---|---|---|---|
| | 40° C. × 30 min. | | 100° C. × 30 min. | |
| | % decrease in wt. | Appearance | % decrease in wt. | Appearance |
| Ex. 8 | 1.2 | semi-transparent | 2.8 | slightly cloudy |
| Ex. 2 | 0.8 | semi-transparent | 2.3 | slightly cloudy |
| Ex. 7 | 1.5 | semi-transparent | 4.7 | slightly cloudy |
| Ex. 9 | 1.1 | semi-transparent | 2.9 | slightly cloudy |
| Ex. 10 | 1.4 | semi-transparent | 3.5 | slightly cloudy |
| Ref. 1* | 2.3 | slightly cloudy | 9.8 | cloudy |
| Ref. 2* | 4.3 | cloudy | 15.2 | " |
| Ref. 4 | 2.7 | slightly cloudy | 11.5 | " |
| None | 100.0 | completely dissolved | 100.0 | completely dissolved |

*The resulting film was not homogeneous because of poor compatibility of the cross-linking agent with the PVA solution.

EXAMPLE 16

Cross-linking of methylcellulose

A 10% aqueous solution of methylcellulose (methoxy group content 28–30%, hydroxypropoxy content 7–12%) was mixed with a solution of blocked urethane prepolymer obtained in the preceding examples at a ratio of 100:10 on dry basis.

A cross-linked film was prepared from this mixture and tested as in Example 15. The results are shown in Table VI.

TABLE VI

| Cross-linking agent | Soaking in water at 40° C. for 60 min. | | |
|---|---|---|---|
| | % decrease in wt. | Appearance | |
| | | Before soaking | After soaking |
| Ex. 8 | 2.4 | semi-transparent, flexible | slightly cloudy |
| Ex. 2 | 1.8 | semi-transparent, flexible | slightly cloudy |
| Ex. 7 | 2.1 | semi-transparent, flexible | slightly cloudy |
| Ex. 9 | 1.4 | semi-transparent, flexible | slightly cloudy |
| Ex. 10 | 1.6 | semi-transparent, flexible | slightly cloudy |
| None | 100.0 | semi-transparent, rigid | completely dissolved |

EXAMPLE 17

A 10% aqueous solution of carboxymethylstarch (degree of substitution 0.6 per glucose unit) was mixed with a solution of blocked urethane prepolymer prepared in the preceding examples at a varying ratio on dry basis.

A cross-linked film was prepared from this mixture and tested as in Example 15. The results are shown in Table VII.

TABLE VII

| Cross-linking agent | Amount*[1] | % decrease in weight after soaking in water at 60° C. for 30 min. |
|---|---|---|
| Ex. 8 | 10 | 27.3 |
| | 15 | 14.0 |
| | 20 | 8.8 |
| Ex. 2 | 10 | 16.5 |

TABLE VII-continued

| Cross-linking agent | Amount[*1] | % decrease in weight after soaking in water at 60° C. for 30 min. |
|---|---|---|
|  | 15 | 11.4 |
|  | 20 | 6.3 |
| Ex. 7 | 10 | 22.1 |
|  | 15 | 15.7 |
|  | 20 | 9.4 |
| Ex. 9 | 10 | 19.2 |
|  | 15 | 11.0 |
|  | 20 | 5.5 |
| Ref. 1[*2] | 20 | 17.9 |
| Ref. 2[*2] | 20 | 45.2 |
| Ref. 3 | 20 | 22.7 |

[*1]Parts per 100 parts of CM starch on dry basis.
[*2]The resulting film was not homogeneous.

EXAMPLE 18

Cross-linking of acrylic resin

A reactive acrylic emulsion (hydroxyethyl ester-containing polymer, non-volatile content 45%) was mixed a solution of blocked urethane prepolymer at a varying ratio. A cross-linked film was prepared as in Example 15 and tested on the water-resistance and solvent-resistance, respectively. The results are shown in Table VIII.

TABLE VIII

| Cross-linking agent | Amount[*1] | Water-[*2] resistance (%) | Solvent-[*3] resistance (%) |
|---|---|---|---|
| Ex. 8 | 5 | 13 | 170 |
|  | 10 | 10 | 83 |
| Ex. 2 | 5 | 12 | 160 |
|  | 10 | 9 | 74 |
| Ex. 7 | 5 | 15 | 180 |
|  | 10 | 10 | 115 |
| Ex. 9 | 5 | 11 | 130 |
|  | 10 | 6 | 67 |
| None | — | 28 | 495 |

[*1]Parts per 100 parts of acrylic resin on dry basis.
[*2]Percent increase in area after soaking in water at room temperature for 24 hours.
[*3]Percent increase in area after soaking in methyl ethyl ketone at room temperature for 24 hours.

EXAMPLE 19

Cross-linking of polyether-polyol

An adduct of a 70:30 mixture of ethylene oxide and propylene oxide with glycerine (average M.W.=3,300) was mixed with a solution of blocked urethane prepolymer prepared in the preceding examples at an effective NCO/OH ratio of 1.0. A cross-linked film was prepared from the mixture as in Example 15 and tested on the water-resistance. The results are shown in Table IX.

TABLE IX

| Run No. | 1 | 2 | 3 | 4 | 5 | 6 |
|---|---|---|---|---|---|---|
| Polyether polyol, parts | 100 | 100 | 100 | 100 | 100 | 100 |
| Cross-linking agent, (% N.V.), parts | — | Ex. 8 (30%) 219.6 | EX. 2 (20%) 251.5 | Ex. 7 (20%) 181.4 | Ex. 9 (30%) 104.5 | Ex. 10 (30%) 139.4 |
| 5% dibutyltin dilaurate, parts | — | 17.6 | 20.1 | 14.5 | 8.3 | 11.2 |
| 5% NaHCO3 | — | 6.6 | 7.5 | 5.4 | 3.1 | — |
| Film appearance | viscous liquid | semi-rigid resilient film | flexible resilient film | rigid resilient film | rigid resilient film | flexible resilient film |
| Water-resistance* | completely dissolved | 132 | 145 | 114 | 120 | 118 |

*Percent increase in area after soaking in water at room temperature for 24 hours.

EXAMPLE 20

Shrink-proof treatment of cotton fabric

A scoured 100% cotton fabric was soaked in a solution of blocked urethane prepolymer prepared in the preceding examples (adjusted at a non-volatile content of 3% and at pH 7) and squeezed to a pick up amount of about 80%. The fabric was dried at 100° C. for 3 minutes and then treated at 170° C. for 2 minutes. The treated fabric was tested on the shrink-proofness according to JIS L-1042 F1. The results are shown in Table X.

TABLE X

| Treating agent | % Shrinkage | |
|---|---|---|
|  | Longitudinal | Lateral |
| Ex. 8 | 0.5 | 0.5 |
| Ex. 2 | 0.5 | 0.5 |
| Ex. 7 | 1.0 | 0.5 |
| Ex. 9 | 0.5 | 0 |
| Untreated | 6.0 | 4.0 |

The above has been offered for illustrative purposes only, and it is not for the purpose of limiting the scope of this invention which is defined in the claims below.

We claim:

1. A thermally reactive, water-soluble and water-stable urethane prepolymer having at least one ionizable group and a plurality of masked isocyanate groups capable of regenerating free isocyanate groups at an elevated temperature, said urethane prepolymer having the formula:

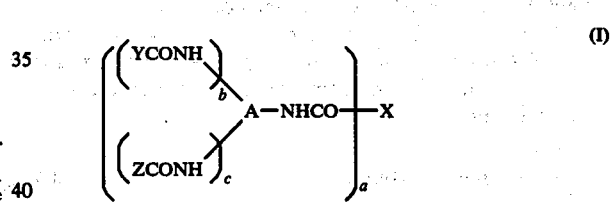

(I)

wherein
A is an organic bridging group having a valence of 3 to 5,
X is the residue having a valence of 2 to 4 of an active hydrogen compound having a corresponding number of reactive hydrogen atoms, after removal of said reactive hydrogen atoms,
Y is a masking group for the masked isocyanate group,
Z is the residue of a compound having at least one reactive hydrogen atom and at least one ionizable group, after removal of said at least one reactive hydrogen atom, a is the integer 2, 3 or 4, and b and c are such that the sum of b+c equals 2, 3 or 4 and the products ab and ac are at least 2 and at least 1, respectively.

2. A urethane prepolymer of claim 1 wherein X is the residue, lacking a reactive hydrogen atom, of a polyol, a polyamine, an amino alcohol, a polyester-polyol, a polybutadiene-polyol, a polychloroprenepolyol, a polyether-polyol, a polythioether, a polyacetal, a polyester-amide or an acrylic polyol.

3. A urethane prepolymer of claim 2 wherein X is the residue of trimethylolpropane, ethylenediamine, polybutadiene glycol (average M.W.=3,000), an ethylene oxide adduct of bisphenol A (2:1 molar ratio, OH number=35.4), a polyether-polyol (average M.W.=500) or 1,6-hexanediolmaleate glycol.

4. A urethane prepolymer of claim 1 wherein Y is the residue, lacking a reactive hydrogenation, of a phenol, a secondary or tertiary alcohol, an oxime, a lactam, an active methylene compound, a heterocyclic hydroxyl compound, or a bisulfite.

5. A urethane prepolymer of claim 1 wherein the ionizable group in Z is a carboxylate group, a sulfonate group or a quaternary ammonium group.

6. A urethane prepolymer of claim 1, wherein Z is the residue, lacking a reactive hydrogen atom, of taurine, sodium glycinate, or N,N-diethylethanolamine.

7. A process for preparing a urethane prepolymer of claim 1, which comprises the steps of:

(a) reacting a polyisocyanate having 3 to 5 isocyanate groups with an active hydrogen compound having 2 to 4 active hydrogen atoms, to produce a urethane prepolymer of the formula:

(II)

wherein all symbols are as defined for Formula (I), (b) reacting the thus-produced urethane prepolymer with a masking agent to produce a partially blocked urethane prepolymer of the formula:

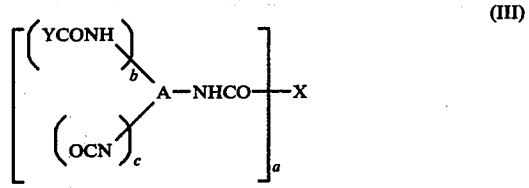

(III)

wherein all symbols are as defined for Formula (I), (c) reacting the thus-produced partially blocked urethane prepolymer with a compound having at least one hydrogen atom and at least one ionizable group, to produce the urethane prepolymer of Formula (I).

8. The process of claim 7, wherein said polyisocyanate is tris-(isocyanatohexyl)-biuret, triphenylmethane-triisocyanate, polymethylenepolyphenylpolyisocyanate, an adduct of a diisocyanate with a low molecular weight polyol having 3 to 5 hydroxyl groups, or a trimer of a diisocyanate.

9. The process of claim 8, wherein said reactive hydrogen compound is a polyol, a polyamine, an amino alcohol, a polyester-polyol, a polybutadiene-polyol, a polychloroprenepolyol, a polyether-polyol, a polythioether, a polyacetal, a polyester-amide or an acrylic polyol.

10. The process of claim 9, wherein said masking agent is a phenol, a secondary or tertiary alcohol, an oxime, a lactam, an active methylene compound, a heterocyclic hydroxyl compound, or a bisulfite.

11. The process of claim 9, wherein said ionizable group is a carboxylate group, a sulfonate group or a quaternary ammonium group.

12. The process of claim 11, wherein said compound used in step (c) further contains at least one primary or secondary amino group, or a hydroxyl group.

* * * * *